US00PP22521P2

(12) United States Plant Patent
Dickerson

(10) Patent No.: US PP22,521 P2
(45) Date of Patent: Feb. 28, 2012

(54) ***VACCINIUM* PLANT NAMED 'CORABLUE'**

(50) Latin Name: ***Vaccinium* spp.**
Varietal Denomination: CORABLUE

(76) Inventor: David Dickerson, Hawthorne, FL (US)

( * ) Notice: Subject to any disclaimer, the term of this patent is extended or adjusted under 35 U.S.C. 154(b) by 0 days.

(21) Appl. No.: 12/802,264

(22) Filed: Jun. 3, 2010

(51) Int. Cl.
*A01H 5/00* (2006.01)

(52) U.S. Cl. ..... Plt./157
(58) Field of Classification Search ..... Plt./157
See application file for complete search history.

*Primary Examiner* — June Hwu
(74) *Attorney, Agent, or Firm* — Cassandra Bright

(57) ABSTRACT

A new and distinct *Vaccinium* spp. cultivar named 'CORABLUE' is disclosed, characterized by a compact plant habit, vigorous growth and glossy leaves. The new variety shows tolerance for a wide variety of soil moisture conditions, including drought. The new variety is a *Vaccinium,* and is normally used as an ornamental garden or landscape plant.

2 Drawing Sheets

Figure 1:
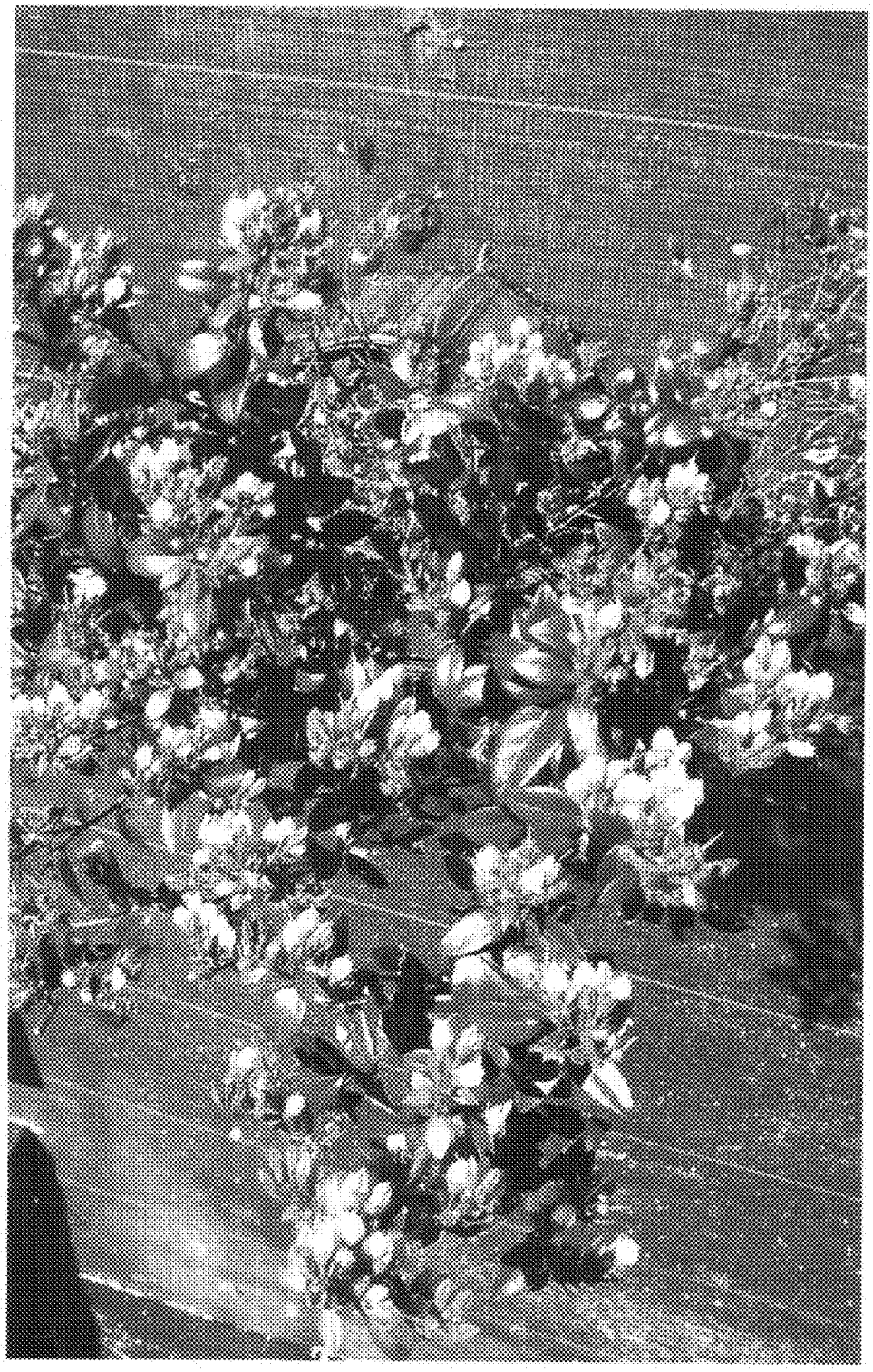

Latin name of the genus and species: *Vaccinium* spp.
Variety denomination: 'CORABLUE'.

BACKGROUND OF THE INVENTION

The new cultivar was discovered as a chance seedling, in a commercial nursery in Hawthorne, Fla. The inventor, David Dickerson, a citizen the United States, discovered the new variety as a seedling among several plants of the unpatented varieties, *Vaccinium myrsinites* and *Vaccinium corymbosum.* The new variety was discovered in May of 2006 by the inventor. After discovery the inventor observed and propagated the variety in the controlled environment of his nursery in Hawthorne Fla. After approximately 3 years of observation, the inventor noted characteristics of both *Vaccinium myrsinites* and *Vaccinium corymbosum* in the new variety. For this reason, the inventor believes, to the best of his knowledge, the new variety to be an inter-specific cross between *Vaccinium myrsinites* and *Vaccinium corymbosum.* This is not a known fact as the new variety is the result of a chance crossing rather than a controlled crossing.

Asexual reproduction of the new cultivar 'CORABLUE' by vegetative cuttings was performed at the nursery in Hawthorne, Fla. in September of 2007. Vegetative reproduction by cuttings has produced multiple generations, and has shown that the unique features of this cultivar are stable and reproduced true to type through successive generations.

SUMMARY OF THE INVENTION

The cultivar 'CORABLUE' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'CORABLUE.' These characteristics in combination distinguish 'CORABLUE' as a new and distinct *Vaccinium* spp. cultivar:

1. Compact plant habit, suitable for ornamental garden use.
2. Improved drought tolerance.
3. Improved soil moisture tolerance.

4. Unique glossy leaves.
5. Vigorous growth habit.

PARENT COMPARISON

Plants of the new cultivar 'CORABLUE' are similar to plants of the parent variety *Vaccinium corymbosum* in most horticultural characteristics. However, plants of the new cultivar 'CORABLUE' form more compact plants, for improved ornamental garden performance. Additionally, the new variety tolerates drought better than the parent variety and has smaller, glossier leaves than *Vaccinium corymbosum.*

Plants of the new cultivar 'CORABLUE' are similar to plants of the parent variety *Vaccinium myrsinites* in most horticultural characteristics. However, plants of the new cultivar 'CORABLUE' have better moisture tolerance and more vigor. Additionally, the new variety has larger, glossier leaves than *Vaccinium myrsinites.*

COMMERCIAL COMPARISON

In addition to the parent varieties, 'CORABLUE' can also be compared to the unpatented commercial variety *Vaccinium darrowii* 'Rosa's Blush.' Plants of the new variety are similar to 'Rosa's Blush' in most horticultural characteristics, however, 'CORABLUE' has significantly more flexible stems than 'Rosa's Blush, preventing unwanted breakage.

BRIEF DESCRIPTION OF THE PHOTOGRAPH

The accompanying photograph in FIG. 1 illustrates in full color a typical flowering plant of 'CORABLUE' grown outdoors in Hawthorne, Fla., with older, glossy dark green foliage. This plant is approximately 18 months old.

Figure 2:
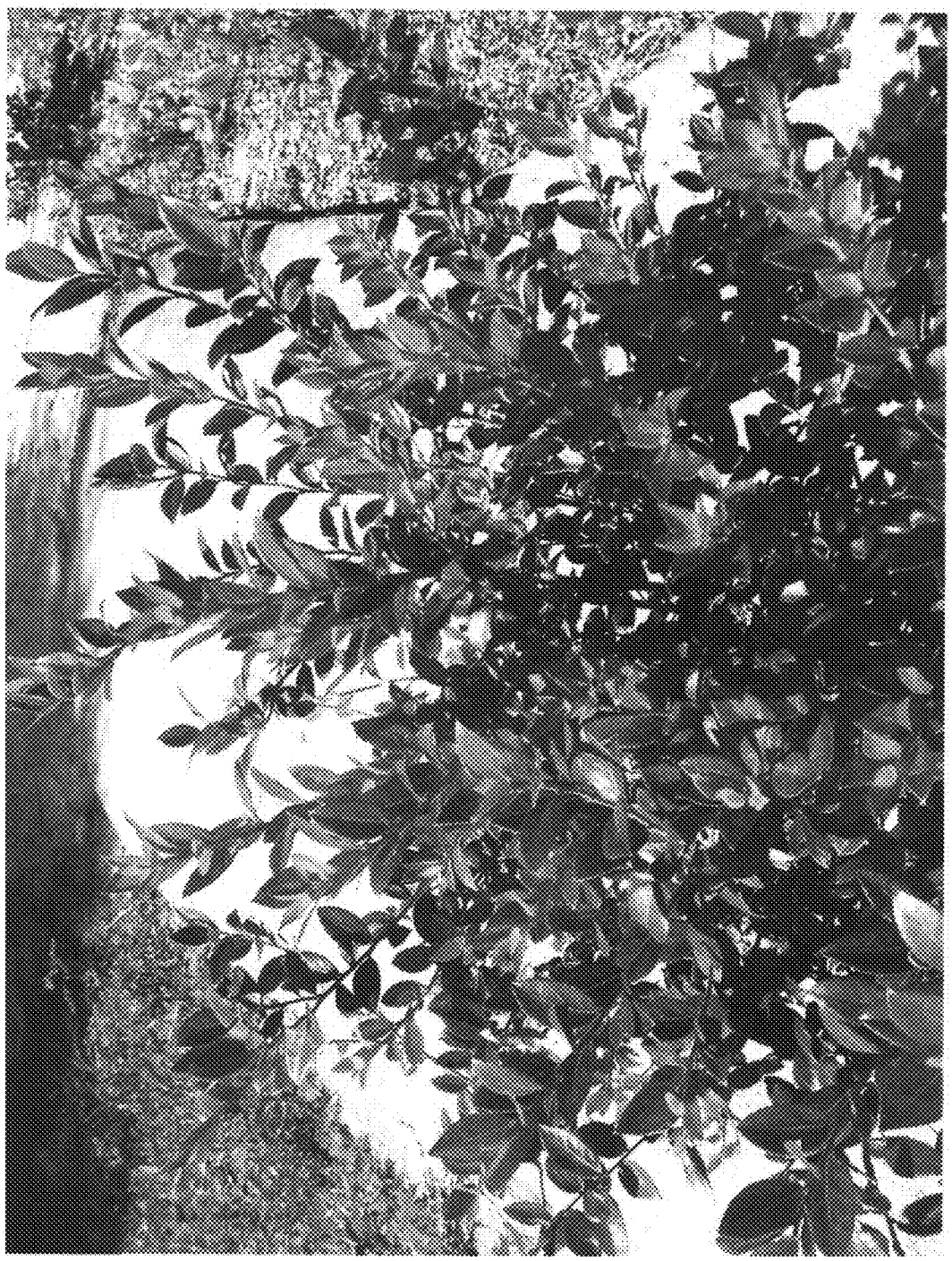

FIG. 2 illustrates in full color a typical plant of 'CORABLUE' with the characteristically red foliage color of the new growth.

The plant is approximately 1 year old. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'CORABLUE' plants grown outdoors in Hawthorne, Fla. Year round temperature ranged from approximately 16 to 100° F., with naturally high light conditions. Measurements and numerical values represent averages of typical flowering types. No chemical or photoperiodic treatments were given.

Botanical classification: *Vaccinium* spp. 'CORABLUE'

Age of plant described: Approximately 1 years old, planted in a 1 gallon container.

PROPAGATION

Typically from semi-hardwood juvenile cuttings.

PLANT

Growth habit: Semi-upright deciduous woody perennial shrub.

Height: Approximately 45 cm, from soil line.

Plant spread: Approximately 60 cm.

Growth rate: Moderate to rapid.

Branching characteristics: Free branching.

Texture of lateral branches: Smooth.

Color of lateral branches: Immature: Near RHS Yellow-Green 144C with flushing near RHS Greyed-Red 180B.

Aspect: Straight, occurring at approximately 15° angle,

Strength of lateral branches: Very strong, very flexible.

FOLIAGE

Leaf:

*Arrangement.*—Alternate.

*Average length.*—Approximately 6 cm.

*Average width.*—Approximately 2.4 cm.

*Shape of blade.*—Broad elliptic.

*Apex.*—Acute.

*Base.*—Obtuse.

*Attachment.*—Stalked.

*Margin.*—Entire.

*Texture of top surface.*—Highly glossy, glabrous.

*Texture of bottom surface.*—Smooth, matte.

*Leaf internode length.*—Approximately 1.5 cm.

*Color.*—Young foliage upper side: Near RHS Greyed-Purple 185A. Young foliage under side: Near RHS Yellow-Green N144A with strong flushing near Greyed-Purple 184B. Mature foliage upper side: Near RHS Green 135B. Mature foliage under side: Near RHS Green 137B. Fall foliage upper side: Near RHS Green 135B with flushing Red-Purple 60B. Fall foliage under side: Near RHS Green 137B with flushing Red-Purple 59A.

*Venation.*—Type: Pinnate. Venation color upperside: Near RHS Green 143B. Venation color underside: Near RHS Green 143A.

*Petiole.*—Length: Approximately 0.2 cm. Diameter: Approximately 0.2 cm. Texture: Smooth. Color upperside: Near RHS Greyed-Purple 184A with flushing near Green 143C. Color underside: Near RHS Green 143B with flushing near Greyed-Purple 184B.

FLOWER

Natural flowering season: Winter to early Spring

Inflorescence and flower type and habit: Urceolate racemes

Quantity of flowers per raceme: Approximately 10 to 15 open flowers and 10 to 15 buds per raceme.

Diameter of raceme: Average approximately 12 cm

Depth of raceme: Average approximately 8 cm

Lastingness: Approximately 1 week.

Fragrance: Not observed.

Bud:

*Shape.*—Obovate.

*Length.*—Approximately 1.0 cm.

*Diameter.*—Approximately 0.8 cm.

*Color.*—Near RHS Red-Purple 64D.

Flower size:

*Diameter.*—Approximately 0.8 cm.

*Length.*—Approximately 1.1 cm.

*Corolla tube length.*—Approximately 0.9 cm.

*Aspect.*—Drooping.

Petals:

*Quantity.*—5.

*Arrangement.*—Fused.

*Length.*—Approximately 0.8 cm.

*Width.*—Approximately 0.3 cm.

*Shape.*—Completely fused, no individual shape.

*Apex.*—Acute.

*Base.*—Fused.

*Margin.*—Entire.

*Texture, upper and lower surfaces.*—Shiny.

*Color.*—When opening, outer surface: Near RHS Red-Purple 65A. When opening, inner surface: Near RHS Red-Purple 65C. Fully opened, outer surface: Near RHS Red-Purple 65D. Fully opened, inner surface: Near RHS Red-Purple 65D.

Calyx:

*Sepal quantity.*—5.

*Arrangement.*—Fused.

*Length.*—Approximately 0.5 cm.

*Width.*—Approximately 0.2 cm.

*Shape.*—Deltoid.

*Apex.*—Acute.

*Base.*—Fused.

*Margin.*—Entire.

*Texture, upper and lower surfaces.*—Shiny.

*Color.*—When opening, outer surface: Near RHS Red-Purple 63B. When opening, inner surface: Near RHS Red-Purple 63B.

Pedicels:

*Length.*—Approximately 0.3 cm.

*Diameter.*—Approximately 0.1 cm.

*Strength.*—Weak to moderate.

*Texture.*—Shiny.

*Color.*—Near RHS Red-Purple 63A.

Peduncles:

*Length.*—Approximately 4 cm.

*Diameter.*—Approximately 0.8 cm.

*Strength.*—Moderate.

*Texture.*—Shiny.

*Color.*—Near RHS Yellow-Green 144C with flushing near RHS Red-Purple 63B.

REPRODUCTIVE ORGANS

Stamens:

*Number.*—Typically 10.

*Color.*—Near RHS Yellow 7C.

*Length.*—Approximately 0.3 cm.

Pistil:

*Number.*—1.

*Length.*—Approximately 0.9 cm.

*Style.*—Length: Approximately 0.5 cm. Color: Near RHS Yellow-Green 145B.

*Stigma.*—Shape: Narrowly conical. Color: Near RHS Yellow-Green 153D. Ovary Color: Near RHS Yellow-Green 145A.

Fruit

*Seasonal timing.*—Approximately mid May in Central Florida.

*Color.*—Near RHS Purple N79A.

*Diameter.*—Average 1.2 cm. Other Characteristics of Fruit not observed, variety is intended as a landscape plant, rather than for the fruiting value.

OTHER CHARACTERISTICS

Disease resistance: Resistance to normal foliar diseases normal to *Vaccinium,* have been observed in this variety.

Drought tolerance and temperature tolerance: Low temperature tolerance to approximately USDA Zone 4. Tolerates high temperature extremely well, to at least 40° C. Some drought tolerance. Plants can be allowed in dry soil for several days without damage.

What is claimed is:

1. A new and distinct cultivar of *Vaccinium* plant named 'CORABLUE' as herein illustrated and described.

* * * * *